United States Patent [19]
Oxman et al.

[11] Patent Number: 5,662,886
[45] Date of Patent: Sep. 2, 1997

[54] ADHESIVE AMALGAM SYSTEM

[75] Inventors: Joel David Oxman, Minneapolis; Jon Wallace Fundingsland, Maplewood, both of Minn.

[73] Assignee: Minnesota Mining and Manufacturing Company, St. Paul, Minn.

[21] Appl. No.: 638,614

[22] Filed: Jan. 8, 1991

[51] Int. Cl.$^6$ .................................................. A61K 6/05
[52] U.S. Cl. ........................... 424/49; 424/618; 424/644; 523/109; 523/116; 523/118; 106/35; 420/526; 420/527; 433/226; 433/228.1
[58] Field of Search .................... 424/49, 618, 644; 420/526, 527; 433/226, 228.1; 106/35

[56] References Cited

U.S. PATENT DOCUMENTS

| | | | |
|---|---|---|---|
| 2,991,176 | 7/1961 | Clancy . | |
| 3,513,123 | 5/1970 | Saffir . | |
| 3,574,943 | 4/1971 | Nicholson . | |
| 3,676,112 | 7/1972 | Muhler . | |
| 3,997,328 | 12/1976 | Greener | 420/527 |
| 4,001,483 | 1/1977 | Lee . | |
| 4,064,629 | 12/1977 | Stoner et al. | 433/226 |
| 4,255,192 | 3/1981 | Burns . | |
| 4,453,977 | 6/1984 | Burns et al. | 420/527 |
| 4,528,034 | 7/1985 | Sato et al. | 420/527 |
| 4,645,456 | 2/1987 | James | 433/228.1 |
| 4,664,629 | 5/1987 | Chodkowski | 433/228.1 |
| 4,684,347 | 8/1987 | Phalaghias | 420/527 |
| 4,719,149 | 1/1988 | Aasen et al. | 433/226 |
| 4,859,240 | 8/1989 | Parker | 433/228.1 |
| 4,859,412 | 8/1989 | Grell . | |
| 4,923,400 | 5/1990 | Suzuki et al. | 433/226 |
| 5,049,190 | 9/1991 | Göbel et al. | 106/35 |

FOREIGN PATENT DOCUMENTS

| | | |
|---|---|---|
| 0 291 944 | 11/1988 | European Pat. Off. . |
| 0 413 174 | 2/1991 | European Pat. Off. . |
| 55-22545 | 6/1980 | Japan . |

OTHER PUBLICATIONS

M. Staninec and M. Holt, Journal of Prosthetic Dentistry (1988), vol. 59, p. 397–402.

A. Lacy and M. Staninec, Quintessence International (1989), vol. 20, p. 521–524.

*Restorative Dental Materials*, edited by Robert G. Craig, Ph.D., Eighth Edition, The C.V. Mosby Company (1989) pp. 227–228.

Y. Torii et al., Operative Dentistry (1989), vol. 14, pp. 142–148.

M. Staninec, Quintessence International (1989), vol. 20, pp. 347–351.

*Primary Examiner*—Amy Hulina
*Attorney, Agent, or Firm*—Gary L. Griswold; Walter N. Kirn; Dale A. Bjorkman

[57] ABSTRACT

A modified amalgam composition forming an adhesive bond with tooth structure treated with a dental adhesive. The modified amalgam can be prepared by admixing particulate additives into conventional amalgam alloy powder to form a modified alloy powder and then triturating the modified alloy powder with mercury. The modified amalgam when applied to a prepared tooth cavity that has been precoated with an acrylate- or methacrylate-functional dental adhesive results in an adhesive bond between the modified amalgam and coated tooth structure. Preferred particulate additives for the amalgam alloy powder are acrylate- or methacrylate-functional polymers, metal salts of acrylates or methacrylates, nonmetallic fillers, oxidizing agents and reducing agents.

6 Claims, No Drawings

ADHESIVE AMALGAM SYSTEM

BACKGROUND OF THE INVENTION

1. Field of the Invention

The present invention relates to amalgam compositions for restorative dental repair.

2. Description of the Prior Art

Dental amalgam has been available to the dental profession for well over a century and it is used extensively for intracoronal and extracoronal restorations. Amalgam is highly durable and the strength and occlusal wear characteristics of alternative materials such as composite resins are generally compared to that of amalgam. However, amalgam does not adhere to tooth structure and the dentist must take great care to prepare the tooth cavity with dovetails and various cutout grooves which in effect mechanically lock the amalgam into the cavity. Such required preparation by the dentist results in the need to excavate more tooth structure than would otherwise be necessary if the amalgam were adhesive. This of course weakens the tooth. Additionally the problem of microleakage at the interface of the amalgam and cavity wall tends to occur for a period after the amalgam has been placed into the cavity. Microleakage allows penetration of bacteria, soluble salts and saliva into any space between the amalgam restoration and cavity walls. This can lead to inflammation and pulp irritation which in turn can cause other complications. The penetration of bacteria into spaces between the amalgam and cavity wall can demineralize the cavity walls and lead to formation of recurrent caries. Corrosion of amalgam can cause one of the amalgam alloy metals, for example tin, to deposit along the amalgam and cavity wall interface. This usually leads to tooth discoloration along the interface and can noticeably detract from the esthetic appearance of tooth and restoration. An adhesive seal between amalgam restoration and cavity walls could prevent microleakage. An adhesive amalgam could significantly reduce the amount of tooth the dentist needs to excavate in order to prepare the cavity for restoration. An adhesive amalgam could, impart significantly more strength to the filled tooth structure.

The concept of making an adhesive amalgam is thus attractive from many standpoints. Unfortunately the nature of amalgam and teeth makes it very difficult to adhere amalgam to tooth structure.

U.S. Pat. No. 3,513,123 (Saffir) discloses an epoxy liquid resin composition which is added to amalgam in and effort to make the amalgam adhere to tooth structure. This reference discloses use of an epoxy liquid resin additive consisting of a glycidyl ether type epoxy resin containing a polyamine hardening agent.

Various references disclose mixtures of amalgam with various additives to impart improved mechanical characteristics. For example U.S. Pat. No. 4,859,412 (Grell) discloses the addition of ceramic or glass powder to alloy powder, which when amalgamated with mercury, produces an amalgam with improved mechanical strength properties. Japanese patent publication 55-22545 discloses use of glass additives which can be blended with amalgam during the amalgamation of alloy powder with mercury. The amalgam modified with glass additives is alleged to impart improved compressive strength properties.

U.S. Pat. No. 2,991,176 (Clancy) discloses mixtures of silica powder, alumina and other materials with amalgam alloy powder. The amalgam alloy powder and other materials are milled to form particles wherein these materials are encapsulated by the amalgam alloy powder. When the encapsulated particles are amalgamated with mercury, a modified amalgam is formed and is said to have reduced thermal coefficient of expansion which in turn reduces the chance for microleakage.

U.S. Pat. Nos. 4,255,192 (Burns), 4,684,347 (Palaghias) and 3,676,112 (Muhler) disclose modified amalgams which utilize various additives or treatment of the amalgam alloy powder to impart varying physical or cariostatic properties to the amalgam.

U.S. Pat. No. 4,064,629 (Stoner), discloses a method for applying amalgam restorations which involves precoating the surfaces of a cavity within a carious tooth with a layer of an "adhesive-metal" lining composition. The metal of the lining composition is amalgamated by diffusion of the mercury from the subsequently applied conventional dental amalgam filling. The "adhesive-metal" lining composition is said to improve corrosion resistance of the dental amalgam filling and also promotes bonding between the amalgam restoration and the cavity surfaces. Other references which disclose precoating the surfaces of a tooth cavity with an adhesive coating said to adhere to conventional amalgam are, for example, U.S. Pat. Nos. 4,001,483 (Lee) and 3,574,943 (Nicholson).

In recent years several adhesive products which claim to make amalgam adhesive to tooth structure have been made available to dental clinicians. (The term "tooth structure" as used hereinafter shall be interpreted to include either or both dentin and enamel, optionally precoated with liner or base.) One such product is sold in a kit form under the trademark "AMALGAMBOND" available from Parkell Co. The "AMALGAMBOND" product is a liquid adhesive resin which is coated directly onto tooth structure. The application and curing procedure are cumbersome and involve a number of steps. The curing procedure also requires use of an air-sensitive catalyst which if dropped on flammable paper causes smoldering. The active ingredients in the adhesive are 4-META (4-methacryloxyethyl trimellitic anhydride) and TBB (tri-n butyl borane). Other products which similarly involve coating a specific curable resin directly onto tooth structure to make amalgam adhere are available under the trademarks "PANAVIA" Dental Adhesive from Kuraray Company and "SUPERBOND" Adhesive from Sun Medical Co., Ltd., Kyoto, Japan. These latter products also are difficult to employ, since there are a number of required preparatory steps for their application and curing.

Literature articles which disclose bonding of amalgam to tooth structure by precoating the tooth with adhesive resin include M. Staninec and M. Holt, *Journal of Prosthetic Dentistry* (1988), Vol. 59, p. 397–402, A. Lacey and M. Staninec, *Quintessence International* (1989), vol. 20, p. 521–524, and Y. Torii, et al. *Operative Dentistry* (1989), Vol. 14, p. 142–148. The above listed articles report improved adhesive tensile strength between amalgam and coated tooth structure but do not report adhesive shear bond strength of the amalgam.

SUMMARY OF THE INVENTION

The present invention is directed in principal aspect to a modified amalgam composition which produces an adhesive bond with treated tooth structure. In the preferred embodiments the tooth structure is coated with an acrylate- or methacrylate-functional dental adhesive.

The modified amalgam of the invention is produced by admixing particulate additives into conventional amalgam. A modified amalgam of the invention can be produced, for example, by admixing particulate additives into "DISPERSALLOY" alloy powder. The modified amalgam is then prepared in a conventional manner by triturating the modified alloy powder with mercury in an amalgamator. The modified amalgam when applied to a prepared tooth cavity which has been precoated with acrylate- or methacrylate-functional dental adhesive results in an adhesive bond between the modified amalgam and the coated tooth structure. Since the modified amalgam adheres to the coated tooth structure, the dentist generally will not need to excavate as much tooth structure in preparing the cavity as would be necessary when placing a conventional unmodified amalgam restoration. This results in a saving of tooth structure and reduces the chance of the tooth weakening because of the cavity preparation. Also, the present invention significantly reduces the chance of microleakage occurring at the interface between the amalgam and cavity walls, since the adhesive bond between amalgam and tooth structure discourages penetration of bacteria, soluble salts and saliva between the amalgam restoration and cavity walls.

The preferred particulate additives which can be admixed into conventional amalgam to produce the modified amalgam of the invention are selected from the following groups: 1) acrylate- or methacrylate-functional polymers, 2) metal salts of acrylates or methacrylates, 3) nonmetallic fillers, 4) oxidizing agents, and 5) reducing agents.

DETAILED DESCRIPTION

A preferred embodiment of the present invention is a restorative system for making amalgam adherent to tooth structure. The system of the invention involves production of a modified formulation for amalgam and employing that modified formulation in combination with dental adhesive applied to tooth structure. The modified amalgam composition of the invention involves adding a particulate material, preferably nonmetallic particulate material in powder form, to conventional dental amalgam alloy powder. As is well known, conventional amalgam preparations are available in capsules which contain amalgam alloy powder and mercury, sealed by a penetrable bladder located at one end of the capsule. A small metal rod is included in the capsule. The clinician prepares amalgam by placing the capsule containing the alloy powder and mercury into an amalgamator. The amalgamator, (or triturator as it is often called), vibrates at high speed so that the metal rod within the capsule can penetrate the bladder to release the mercury contained therein. As mercury admixes into the alloy powder a reaction occurs between alloy powder and mercury and the amalgam slowly begins to set. At this stage the amalgam is ready for packing into the tooth cavity.

The present invention involves the simple addition of a particulate material to conventional amalgam alloy powder. The powder additives of the present invention are intended to be applicable to the full range of conventional amalgam alloy powders and conventional weight ratios of mercury in relation to total amalgam alloy powder. Conventional alloy powders are typically mixtures of silver, tin, copper, and zinc. Conventional amalgam alloy powders have proper proportioning of these metals to result in an alloy described in the art as a "balanced alloy." For example it is known that increasing the silver content increases the expansion of the setting amalgam, shortens setting time, increases compressive strength, and tends to make the alloy mixture more difficult to amalgamate. Tin behaves in an opposite way for all these properties. Copper and zinc contribute properties similar to silver with respect to expansion, setting time and strength, but copper is used principally for increased strength and zinc for increased resistance to tarnish. Conventional alloys are broadly classified as low-copper alloys (5% or less copper) and high copper alloys (13% to 30% copper). Commercially available low copper amalgam alloys contain typically the following compositions which apply to lathe-cut or spherical particle shapes: silver (63–70%), tin (26–28%), copper (2–5%), and zinc (0–2%). Commercially available high copper alloys using lathe-cut particles contain typically the following compositions: silver (40–70%), tin (26–30%), copper (2–5%), and zinc (0–2%). Commercially available high copper alloys using spherical particles contain typically the following compositions: silver (40–65%), tin (0–30%), copper (20–40%), zinc (0%), and palladium (0–1%). Mercury typically represents 40 to 60 percent by weight of the amalgam mix. A widely used high copper amalgam alloy is available under the trademark "DISPERSALLOY" alloy from Johnson & Johnson Company. The "DISPERSALLOY" alloy contains about 13% copper and the mixed "DISPERSALLOY" amalgam contains about 50% mercury.

We have discovered that the particulate additives of the invention when mixed into conventional amalgam alloy powder (preferably high copper alloy powder, e.g. "DISPERSALLOY" alloy powder) provide a modified restorative amalgam that adheres very effectively to tooth structure which has been precoated with a dental adhesive. Representative preferred dental adhesives for the system of the invention are available under the trademark "SCOTCHBOND" Dual Cure Dental Adhesive and "SCOTCHBOND 2" Light Cure Dental Adhesive, both from 3M Dental Products Division. "SCOTCHBOND" Dual Cure Dental Adhesive is described in U.S. Pat. Nos. 4,544,467 (Bunker), 4,670,576 (Bunker), 4,929,746 (Bunker), and 4,669,983 (Bunker). The compounds disclosed in these references include generally acrylate- or methacrylate-functional dental adhesives which bond to tooth structure. The "SCOTCHBOND" Dual Cure Dental Adhesive can be applied to tooth structure and cured with light or under room temperature conditions in the manner described in the "SCOTCHBOND" Dual Cure Dental Adhesive kit.

The composition of the "SCOTCHBOND 2" Light Cure Dental Adhesive is disclosed in U.S. Pat. No. 4,719,149 (Aasen). The "SCOTCHBOND 2" dental adhesive is applied to tooth structure and light cured in the manner described in the "SCOTCHBOND 2" Light Cure Dental Adhesive kit. Both "SCOTCHBOND" and "SCOTCHBOND 2" dental adhesives were commonly intended for bonding various conventional composite restorative resins to tooth structure.

Other preferred dental adhesives which can be employed with the modified amalgam of the present invention contain acrylate- or methacrylate-functional polymers and may also contain phosphorous compounds. In such dental adhesives either a single phosphorus compound or a mixture of phosphorus compounds can be used. Dental adhesives which can be precoated onto tooth structure and used with the modified restorative amalgam of the invention to produce an adhesive bond between the amalgam and tooth structure include "ALL-BOND" Universal Dental Adhesive System from Bisco, Inc., "CLEARFIL" Photo Bond Light Cured Dental Bonding Agent from Kuraray Co., Ltd., "RESTOBOND 3" Dual Dentin-Enamel Bonding Agent from Lee Pharmaceuticals, (see U.S. Pat. Nos. 4,524,527 and 4,521,550), "TENURE" Solution Dentin Bonding System from Den-Mat Corporation, "GLUMA" Bonding System from Columbus Dental Miles, Inc., "PRISMA UNIVERSAL BOND 2" Dentin/Enamel Bonding Agent from L. D. Caulk Division of Dentsply International, Inc., (see U.S. Pat. No. 4,814,423), "MIRAGE-BOND" Dentin-Enamel Bonding System from Chameleon Dental Products, INC., (see U.S. Pat. Nos. 4,514,527, 4,521,550, 4,588,756, and 5,659,751), "BONDLITE" dental adhesive from Sybron Corp., "Johnson & Johnson" dentin bonding agent and "Johnson & Johnson" light-curing bonding agent, both from Johnson & Johnson Co., "PALFIQUE" bonding agent from Tokuyama Soda Co., Ltd., "SHOFU" bonding base from Shofu, Inc, and "SINTERBOND" dental adhesive from Teledyne Getz. All of the above adhesives are acrylate- or methacrylate-functional dental adhesives.

If desired, other free-radically polymerizable non-phosphorus-containing compounds can be mixed with the dental adhesive, for example, as a diluent to reduce viscosity or promote wetting. Other suitable free-radically polymerizable compounds include mono- or poly- (e.g., di-, tri- or tetra-functional) acrylates and methacrylates such as methyl acrylate, 2-hydroxyethyl acrylate, triethyleneglycol diacrylate, neopentylglycol diacrylate, hexamethyleneglycol diacrylate, trimethylolpropane triacrylate, pentaerythritol tetraacrylate, polyalkylene glycol mono- and di-acrylates, urethane mono- or poly-functional acrylates, Bisphenol A diacrylates, and the corresponding methacrylates of the above compounds, as well as acrylamides and methacrylamides, vinyl compounds, styrene compounds, and other olefinically unsaturated compounds suitable for use in the oral environment. U.S. Pat. Nos. 4,499,251, 4,515,930, 4,537,940 and 4,539,382 contain an extensive list of such compounds.

We have found that the following groups of additives when added to conventional amalgam alloy powder, e.g., "DISPERSALLOY" powder, make the amalgam strongly adherent to tooth structure precoated with an acrylate- or methacrylate-functional dental adhesive.

Group 1—Acrylate- or Methacrylate-Functional Polymers

Representative acrylate- or methacrylate-functional moieties include poly(alkanoic acid) powder. This polymer is a copolymer of itaconic and acrylic acid, and is described in European published patent application No. 88-312127.

Group 2—Metal Salts of Acrylates or Methacrylates

Representative salts from this group include zinc dimethacrylate, zirconium dimethacrylate, silver methacrylate, sodium methacrylate, and magnesium methacrylate.

Group 3—Nonmetallic Fillers

Nonmetallic fillers include both untreated organic fillers and surface-treated fillers. Representative nonmetallic fillers include blends of 66 wt % "OX-50" pyrogenic silica available from Degussa Company, 17 wt % tetraethyleneglycol dimethacrylate ("TEGDMA") from Rohm Tech Co. and 17 wt % diglycidylether dimethacrylate ("BIS-GMA"). (The "OX-50" pyrogenic silica was treated with 20 wt % gamma methacryloxypropyl trimethoxysilane.) The blend is thermally polymerized to a hard mass which is reground to yield a fine powdered filler with particle size less than 50 microns. (The surface of the "OX-50" pyrogenic silica particles could alternatively be treated with gamma-mercaptopropltriethoxysilane or gamma-aminopropyltrimethoxysilane). Other representative nonmetallic fillers include zirconia/silica filler pretreated with gamma-methacryloxypropyl trimethoxysilane as described in U.S. Pat. No. 4,503,169.

Group 4—Oxidizing Agents

Preferred oxidizing agents include benzoyl peroxide.

Group 5—Reducing Agents

Preferred reducing agents include sodium benzenesulfinate.

The above-listed additives either alone or in any combination are preferably admixed into the amalgam alloy powder. Alternatively, where convenient, the additives can be added to the mercury. These additives may also be admixed into the amalgam prepared from alloy powder and mercury just after trituration.

Examples 1–17 show specific powder additives which we have used to modify the alloy. The amount of mercury used in the amalgam is also shown. The specific additive powder shown in Examples 1–17 was added to "DISPERSALLOY" alloy powder which was contained in a conventional amalgam capsule. The capsule contained mercury protected by a penetrable bladder. The capsule in each case was then closed and vibrated in an amalgamator which upon trituration formed the modified restorative amalgam.

The protocol for preparing the bovine teeth and measuring shear bond strength is as follows. Bovine teeth of similar age and appearance were partially embedded in circular acrylic discs. The exposed portion of each tooth was ground flat and parallel to the acrylic disc using Grade 120 silicon carbide paper-backed abrasive mounted on a lapidary wheel, in order to expose the enamel. During this and subsequent grinding and polishing steps, the teeth were continuously rinsed with water. Further grinding and polishing of the teeth was carried out by mounting Grade 600 silicon carbide paper-backed abrasive on the lapidary wheel. The polished teeth were stored in distilled water, and used for testing within 2 hours after polishing. The polished teeth were removed from the water and dried using a stream of compressed air.

Phosphoric acid etching gel was applied to the exposed enamel for 15 seconds, rinsed with water and dried. "SCOTCHBOND" Dual Cure Adhesive or "SCOTCH-BOND 2" Dental Adhesive as indicated in the Examples, was then applied to the exposed enamel with a brush and blown into a thin film with compressed air and then cured with a "VISILUX" 2 dental curing light. The modified restorative amalgam was then packed onto the precoated bovine tooth structure. The adhesive shear bond strength of the modified amalgam was then measured as described below.

Previously prepared molds made from a 2 mm thick "Teflon" sheet with a 5 mm diameter hole through the sheet were clamped to each polished tooth so that the central axis of the hole in the mold was normal to the polished tooth surface. The hole in each mold was filled with a specific modified amalgam of formulation shown in Table I. The teeth and molds were allowed to stand for about 15 minutes at room temperature, then stored in distilled water at 37° C., for 24 hours. The molds were then carefully removed from the teeth, leaving a molded button of amalgam attached to each tooth.

Adhesive strength was evaluated by mounting the acrylic disk in a holder clamped in the jaws of an "Instron" apparatus with the polished tooth surface oriented parallel to the direction of pull. A loop of orthodontic wire (0.44 mm diameter) was placed around the restorative button adjacent to the polished tooth surface. The ends of the orthodontic wire were clamped in the pulling jaw of the Instron apparatus, thereby, placing the bond in shear stress. The bond was stressed until it or the button failed, using a crosshead speed of 2 mm/min.

Comparative Examples A–D were run using a modified amalgam, but without coating the bovine tooth with dental adhesive. In these Comparative Examples the modified amalgam was prepared by mixing various particulate additives into conventional amalgam alloy powder, e.g. "DIS- PERSALLOY" alloy, and amalgamating the mixture for about 20 seconds. In each Comparative Example the adhesive shear bond strength of the modified amalgam was 0 kg/cm². The modified amalgam fell off the tooth structure before placement in water.

Control A and B were prepared using unmodified amalgam applied to precoated tooth structure. In Control A amalgam prepared using unmodified "DISPERSALLOY" amalgam alloy powder was applied to bovine tooth structure precoated with "SCOTCHBOND" Dual Cure Dental Adhesive. The average shear bond strength was 15 kg/cm². In Control B amalgam prepared using unmodified "DISPERSALLOY" amalgam alloy powder was applied to bovine tooth structure precoated with "SCOTCHBOND 2" Dental Adhesive. The average shear bond strength was 0 kg/cm².

Table I gives a tabular listing of the adhesive shear bond strength of "DISPERSALLOY" amalgam alloy powder modified by the addition of the respective powder additive in each Example given in weight percent of total amalgam. In all cases the amount of mercury present in the total amalgam mix equaled the amount of "DISPERSALLOY" alloy powder present in the mix. The adhesive used to precoat the prepared bovine tooth structure in the manner as above described is also listed in Table I. In all cases except Examples 7, 8 and 14, the adhesive shear bond strength of the modified amalgam of the invention was greater than that of the unmodified (Control A and B) "DISPERSALLOY" amalgam.

TABLE I

ADHESIVE SHEAR BOND STRENGTH OF
MODIFIED AMALGAM APPLIED TO PREPARED TOOTH STRUCTURE

| EXAMPLE NUMBER | TOOTH STRUCTURE ADHESIVE PRECOAT | ADDITIVE TO "DISPERSALLOY" ALLOY POWDER | ADDITIVE IN AMALGAM[1] (WT %) | AVERAGE ADHESIVE SHEAR BOND STRENGTH (kg/cm²) |
|---|---|---|---|---|
| 1 | "SCOTCHBOND" Dual Cure Dental Adhesive | Poly(alkanoic acid) powder[2] | 2.00 | 26 |
| 2 | "SCOTCHBOND" Dual Cure Dental Adhesive | Zinc dimethacrylate | 0.25 | 25 |
| 3 | "SCOTCHBOND" Dual Cure Dental Adhesive | " | 0.50 | 28 |
| 4 | "SCOTCHBOND" Dual Cure Dental Adhesive | " | 1.00 | 66 |
| 5 | "SCOTCHBOND" Dual Cure Dental Adhesive | " | 2.00 | 50 |
| 6 | "SCOTCHBOND" Dual Cure Dental Adhesive | Zirconium dimethacrylate | 0.5 | 16 |
| 7 | "SCOTCHBOND" Dual Cure Dental Adhesive | " | 1.00 | 13 |
| 8 | "SCOTCHBOND" Dual Cure Dental Adhesive | Silver methacrylate | 0.38 | 13 |
| 9 | "SCOTCHBOND" Dual Cure Dental Adhesive | Organic filler[3] | 0.25 | 55 |
| 10 | "SCOTCHBOND" Dual Cure Dental Adhesive | Organic filler[3] | 0.50 | 72 |
| 11 | "SCOTCHBOND" Dual Cure Dental Adhesive | " | 1.00 | 25 |
| 12 | "SCOTCHBOND" Dual Cure Dental Adhesive | " | 2.00 | 24 |
| 13 | "SCOTCHBOND" Dual Cure Dental Adhesive | Zirconia/silica filler[4] | 1.00 | 19 |
| 14 | "SCOTCHBOND" Dual Cure Dental Adhesive | Zinc glass powder[5] | 2.00 | 7 |
| 15 | "SCOTCHBOND 2" Dental Adhesive | Benzoyl peroxide | 0.16 | 72 |
| 16 | "SCOTCHBOND" Dual Cure Dental Adhesive | Benzoyl peroxide | 0.38 | 43 |
| 17 | "SCOTCHBOND" Dual Cure Dental Adhesive | Sodium benzenesulfinate | 0.38 | 25 |

TABLE I-continued

ADHESIVE SHEAR BOND STRENGTH OF MODIFIED AMALGAM APPLIED TO PREPARED TOOTH STRUCTURE

| EXAMPLE NUMBER | TOOTH STRUCTURE ADHESIVE PRECOAT | ADDITIVE TO "DISPERSALLOY" ALLOY POWDER | ADDITIVE IN AMALGAM[1] (WT %) | AVERAGE ADHESIVE SHEAR BOND STRENGTH (kg/cm$^2$) |
|---|---|---|---|---|
| Comparative A | None | Zinc dimethacrylate | 1.0 | 0 |
| Comparative B | None | Organic filler[3] | 0.5 | 0 |
| Comparative C | None | Zinc glass powder[5] | 2.0 | 0 |
| Comparative D | None | Benzoyl peroxide | 0.38 | 0 |
| Control A | "SCOTCHBOND" Dual Cure Dental Adhesive | None | 0 | 15 |
| Control B | "SCOTCHBOND 2" Dental Adhesive | None | 0 | 0 |

Notes:
[1]Amalgram in all cases contained equal parts by weight mercury and "DISPERSALLOY" alloy powder (before addition of additive), e.g., composition of Comparative Example B was "DISPERSALLOY" alloy powder (49.75 wt %), mercury (49.75 wt %) and organic filler (0.5 wt %).
[2]Poly(alkanoic acid) powder prepared according to Example 11 of European published patent application No. 88-312127.
[3]Organic filler contained 66 wt % "OX-50" pyrogenic silica which has been treated with 20 wt % gamma-methacryloxypropyl trimethoxysilane, 17 wt % TEGDMA and 17 wt % BIS-GMA.
[4]Zirconia/silica filler powder prepared according to Example 1 of U.S. Pat. No. 4,503,169.
[5]Zinc glass powder prepared according to Example 13 of European published patent application No. 88-312127.

While the present invention has been described with respect to specific embodiments it should be appreciated that the invention is not intended to be limited to such embodiments. Chemical species, other than the preferred species within a disclosed class of additives, may be substituted for the preferred without departing from the scope of the invention. Therefore, the present invention is not intended to be limited to the preferred embodiments but rather is defined by the claims and equivalents thereof.

We claim:

1. A dental restorative system comprising a modified amalgam for application to tooth structure in combination with a dental adhesive for application to tooth structure so that at least a portion of the modified amalgam shall contact tooth structure precoated with said dental adhesive, the modified amalgam comprising silver, mercury and particulate additive, said particulate additive having the property of rendering said modified amalgam adherent to said precoated tooth structure, wherein the particulate additive is selected from the group consisting of acrylate- and methacrylate-functional polymers.

2. A dental restorative system comprising a modified amalgam for application to tooth structure in combination with a dental adhesive for application to tooth structure so that at least a portion of the modified amalgam shall contact tooth structure precoated with said dental adhesive, the modified amalgam comprising silver, mercury and particulate additive, said particulate additive having the property of rendering said modified amalgam adherent to said precoated tooth structure, wherein the particulate additive is selected from the group consisting of metal salts of acrylates and methacrylates.

3. A dental restorative system comprising a modified amalgam for application to tooth structure in combination with a dental adhesive for application to tooth structure so that at least a portion of the modified amalgam shall contact tooth structure precoated with said dental adhesive, the modified amalgam comprising silver, mercury and particulate additive, said particulate additive having the property of rendering said modified amalgam adherent to said precoated tooth structure, wherein the particulate additive comprises nonmetallic filler comprising silane-treated pyrogenic silica.

4. A dental restorative system comprising a modified amalgam for application to tooth structure in combination with a dental adhesive for application to tooth structure so that at least a portion of the modified amalgam shall contact tooth structure precoated with said dental adhesive, the modified amalgam comprising silver, mercury and particulate additive, said particulate additive having the property of rendering said modified amalgam adherent to said precoated tooth structure, wherein the particulate additive comprises silanized zirconia/silica filler.

5. A dental restorative system comprising a modified amalgam for application to tooth structure in combination with a dental adhesive for application to tooth structure so that at least a portion of the modified amalgam shall contact tooth structure precoated with said dental adhesive, the modified amalgam comprising silver, mercury and particulate additive, said particulate additive having the property of rendering said modified amalgam adherent to said precoated tooth structure, wherein the particulate additive comprises benzoyl peroxide.

6. A dental restorative system comprising a modified amalgam for application to tooth structure in combination with a dental adhesive for application to tooth structure so that at least a portion of the modified amalgam shall contact tooth structure precoated with said dental adhesive, the modified amalgam comprising silver, mercury and particulate additive, said particulate additive having the property of rendering said modified amalgam adherent to said precoated tooth structure, wherein the particulate additive comprises sodium benzenesulfinate.

* * * * *